(12) United States Patent
Jain

(10) Patent No.: US 10,835,525 B2
(45) Date of Patent: *Nov. 17, 2020

(54) METHOD OF INHIBITING MUTANT C-KIT

(71) Applicant: Arog Pharmaceuticals, Inc., Dallas, TX (US)

(72) Inventor: Vinay K. Jain, Dallas, TX (US)

(73) Assignee: AROG PHARMACEUTICALS, INC., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,190

(22) Filed: Feb. 22, 2019

(65) Prior Publication Data
US 2019/0183880 A1 Jun. 20, 2019

Related U.S. Application Data

(63) Continuation-in-part of application No. 15/862,011, filed on Jan. 4, 2018, now Pat. No. 10,251,877, which
(Continued)

(51) Int. Cl.
*A61K 31/47* (2006.01)
*A61K 31/4709* (2006.01)
*A61K 45/06* (2006.01)

(52) U.S. Cl.
CPC ......... *A61K 31/4709* (2013.01); *A61K 45/06* (2013.01)

(58) Field of Classification Search
CPC .................................................. A61K 31/4709
(Continued)

(56) References Cited

U.S. PATENT DOCUMENTS

| 5,990,146 A | 11/1999 | Boschelli et al. |
| 7,183,414 B2 | 2/2007 | Tom et al. |

(Continued)

FOREIGN PATENT DOCUMENTS

| WO | 1999016755 | 4/1999 |
| WO | 2001040217 A1 | 6/2001 |

OTHER PUBLICATIONS

Tabone et al. "KIT overexpression and amplification in gastrointestinal stromal tunnors(GISTs)," Biochimica et Biophysica Acta, 2005, 1741, pp. 165-172 (Year: 2005).*
(Continued)

*Primary Examiner* — Shengjun Wang
(74) *Attorney, Agent, or Firm* — Edwin S. Flores; Daniel J. Chalker; Chalker Flores, LLP

(57) ABSTRACT

The present invention includes a method of reducing or inhibiting the kinase activity of C-KIT mutant tyrosine kinase activity in a cell or a subject, and the use of such compound for treating mutant C-KIT driven cell proliferative disorder(s) in a subject related to using a compound of the present invention:

(Continued)

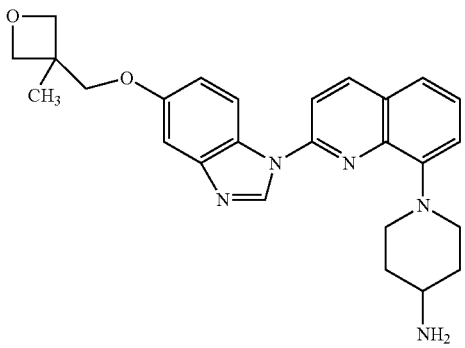

or pharmaceutically acceptable salt thereof.

23 Claims, 11 Drawing Sheets

Related U.S. Application Data is a continuation of application No. 15/255,912, filed on Sep. 2, 2016, now Pat. No. 9,889,127, which is a continuation of application No. 14/026,886, filed on Sep. 13, 2013, now Pat. No. 9,480,683.

(60) Provisional application No. 61/705,838, filed on Sep. 26, 2012.

(58) Field of Classification Search
USPC .......................................................... 514/314
See application file for complete search history.

(56) References Cited

U.S. PATENT DOCUMENTS

| 9,480,683 | B2 | 11/2016 | Jain |
| 9,801,869 | B2 | 10/2017 | Jain |
| 9,889,127 | B2 | 2/2018 | Jain |
| 10,251,877 | B2 | 4/2019 | Jain |
| 2005/0124599 | A1 | 6/2005 | Kath et al. |
| 2013/0230511 | A1 | 9/2013 | Heymach et al. |

OTHER PUBLICATIONS

Akin, et al. "Effects of Tyrosine Kinase Inhibitor STI571 on Human Mast Cells Bearing Wild-type or Mutated C-KIT" Exp Hematol. 2003; 31: 686-692.

Akin, et al. "A Novel Form of Mastocytosis Associated with a Transmembrane C-KIT Mutation and Response to Imatinib" Blood. 2004; 103: 3222-3225.

Broekman, et al. Tyrosine kinase inhibitors: Multi-targeted or single-targeted? World Journal of Clinical Oncology, Feb. 10, 2011, 2(2): 80-93.

Davis, et al. "Comprehensive analysis of kinase inhibitor selectivity" Nat Biotechnol 2011;29:1046-51.

Hayashi, et al. "Effects of Crenolanib, a Highly Selective Platelet-Derived Growth Factor Receptor α/β (PDGFRA/B) Tyrosine Kinase Inhibitor, on the Proliferation of Kii-Mutant Gastrointestinal Stromal Tumor (GIST) Cells and Interstitial Cell of Cajal (ICC) Precursors" Gastroenterology 142(5):S-30 • May 2012.

Heinrich, et al. "The effect of crenolanib (CP-868596) on phosphorylation of the imatinib-resistant D842V PDGFRA activating mutation associated with advanced gastrointestinal stromal tumors" Journal for Clinical Pncology, May 20, 2011, vol. 29, No. 15, Abstract No. 10012.

Heinrich, et al. "Crenolanib Inhibits the Drug-Resistant PDGFRA D842V Mutation Associated with Imatinib-Resistant Gastrointestinal Stromal Tumors" Clinical Cancer Research, published online Jun. 27, 2012, pp. 4375-4384.

Hug, et al. "ETO Interacting Proteins" Oncogene. 2004; 23(24): 4270-4274.

Kunstlinger, et al. "High-resolution melting analysis is a sensitive diagnostic tool to detect imatinib-resistant and Imatinib-sensitive PDGFRA exon 18 mutations in gastrointestinal stromal tumors" Human Pathology (2014) 45, 573-582.

Ma, et al. "The C-KIT Mutation Causing Human Mastocytosis is Resistant to STI571 and Other KIT Kinase Inhibitors; Kinases with Enzymatic Site Mutations Show Different Inhibitor Sensitivity Profiles than Wild-type Kinases and Those with Regulatory-type Mutations" Blood. 2002; 99: 1741-1744.

Miettinen, et al. "KIT (CD117): A Review on Expression in Normal and Neoplastic Tissues, and Mutations and their Clinicopathologic Correlation" Appl Immunohistochem Mol Morphol. 2005; 13: 205-220.

Mok, et al. "Treatment of severe proliferative lupus nephritis: the current state" Ann Rheum Dis 2003; 62: 799-804.

O'Regan, et al. "Gastrointestinal stromal tumors (GIST): lesser known facts" Clinical Imaging (2013) pp. 821-829.

Osaadon, et al. "A review of anti-VEGF agents for proliferative diabetic retinophathy" Eye 2014, 28, 510-520.

Rulina, et al., Biochemistry (Moscow). "Activated Leukemic Oncogenes AML1-ETO and c-kit: Role of Developmen of Acute Myeloid Leukemia and Current Approaches for Their Inhibition" 2010; 75(13): 1650-1666.

Schaefer, et al. "Chromosomal aberrations in primary PDGFRA-mutated gastrointestinal stromal tumors" Human Pathology (2014) 45, 85-97.

Tefferi, et al. "Targeted Therapy in KIT816V-positive mastocytosis: waiting for proof-of-principle. Leukemia and Lymphoma" Mar. 2010; 51(3): 360-362.

Zermati, et al. "Effect of Tyrosine Kinase Inhibitor STI571 on the Kinase Activity of Wild-type and Various Mutated C-KIT Receptors Found in Mast Cell Neoplasms" Oncogene. 2003; 22: 660-664.

* cited by examiner

| | Protein | % of cKIT Activity at 1×10⁻⁷ Crenolanib (No Inhibition) | % Inhibition of cKIT Activity at 1×10⁻⁷ Crenolanib |
|---|---|---|---|
| | cKit | 93.71 | 6.29 |
| Exon 11 (K550-L592) | c-Kit (V559A) | 6.77 | 93.23 |
| | c-Kit (V559D) | 8.89 | 91.11 |
| | c-Kit (V560G) | 6.78 | 93.22 |
| | c-Kit (d557-558) | 5.77 | 94.33 |
| | c-Kit (V559D/T670I) | 17.46 | 82.54 |
| | c-Kit (V559D/V654A) | 25.62 | 74.38 |
| | c-Kit (V560G/D816V) | 2.74 | 97.26 |
| | c-Kit (V560G/N822K) | 5.45 | 94.55 |
| Exon 13 (P627-G664) | c-Kit (K642E) | 36.06 | 63.94 |
| Exon 14 (G664-S714) | c-Kit (V654A) | 91.12 | 8.88 |
| | c-Kit (T670I) | 63.50 | 36.50 |
| | c-Kit (D816E) | 6.60 | 93.40 |
| | c-Kit (D816F) | 10.39 | 89.61 |
| | c-Kit (D816H) | 2.47 | 97.53 |
| Exon 17 (C788-N828) | c-Kit (D816I) | 5.22 | 94.78 |
| | c-Kit (D816V) | 1.29 | 98.71 |
| | c-Kit (D816Y) | 3.65 | 96.35 |
| | c-Kit (D820E) | 9.37 | 90.63 |
| | c-Kit (D820Y) | 4.13 | 95.87 |
| | c-Kit (Y823D) | 13.54 | 86.46 |
| Exon 18 (A829-G866) | c-Kit (A829P) | 20.68 | 79.32 |

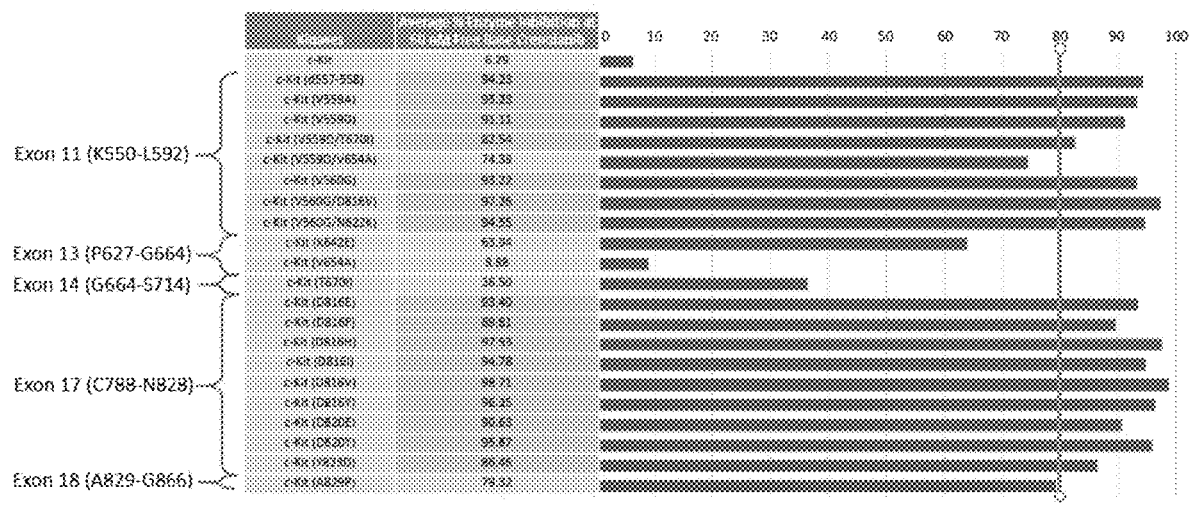
FIGURE 20
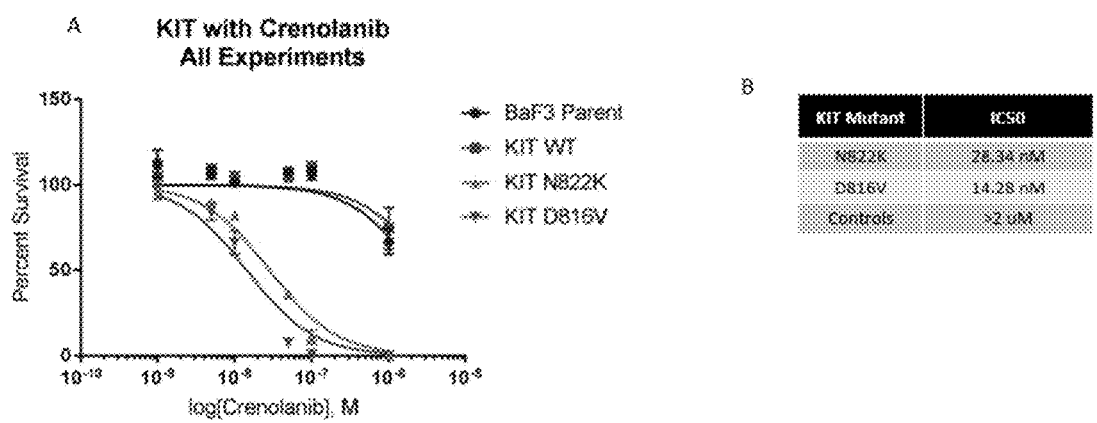
FIGURE 21A
FIGURE 21B

METHOD OF INHIBITING MUTANT C-KIT

CROSS-REFERENCE TO RELATED APPLICATIONS

This application is a continuation-in-part of U.S. patent application Ser. No. 15/862,011 filed on Jan. 4, 2018, now U.S. Pat. No. 10,251,877 issued Apr. 9, 2019 and continuation patent application Ser. No. 15/255,912 filed on Sep. 2, 2016, now U.S. Pat. No. 9,889,127 issued Feb. 13, 2018, which is a continuation of U.S. patent application Ser. No. 14/026,886 filed on Sep. 13, 2013, now U.S. Pat. No. 9,480,683 issued Nov. 1, 2016, which claims priority to U.S. Provisional Application Ser. No. 61/705,838, filed Sep. 26, 2012, the entire contents of which are incorporated herein by reference.

TECHNICAL FIELD OF THE INVENTION

The present invention relates to methods of reducing or inhibiting the kinase activity of mutated C-KIT in a cell or a subject, and the use of such methods for preventing or treating cell disorders related to C-KIT.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with its ability to inhibit the mutant form of KIT in the treatment of KIT dependent diseases.

The c-kit gene is located on locus q11-q12 of the human fourth chromosome and encodes the protein KIT (also known as CD 117), which is a cytokine receptor that is expressed on the surface of a number of different cells. See Rulina et al., Biochemistry (Moscow). Activated Leukemic Oncogenes AML1-ETO and c-kit: Role of Development of Acute Myeloid Leukemia and Current Approaches for Their Inhibition. 2010; 75(13): 1650-1666. KIT is a type III receptor tyrosine kinase of the monomeric receptor family and the transmembrane receptor for stem cell factor. See Tefferi and Pardanani. Leukemia and Lymphoma, March 2010; 51(3): 360-362.

KIT is notably expressed by mast cells, hematopoietic progenitor cells, germ cells, melanocytes, and interstitial cells of Cajal in the gastrointestinal tract and is relevant for normal mast cell development, hematopoiesis, gametogenesis, melanogenesis, and regulation of slow gastric waves. See Miettinen et al. KIT (CD117): A Review on Expression in Normal and Neoplastic Tissues, and Mutations and their Clinicopathologic Correlation. Appl Immunohistochem Mol Morphol. 2005; 13: 205-220.

Activating mutations that give rise to ligand-independent activation of KIT occur in the juxtamembrane and kinase domains of the gene. See Hug et al. ETO Interacting Proteins. Oncogene. 2004; 23(24): 4270-4274. Mutations that lead to an activated form of KIT have been shown to play a role in proliferative disease such as mastocytosis, acute myeloid leukemia, gastrointestinal stromal tumors, sinonasal NK/T-cell lymphoma, seminomas, dysgerminomas, melanomas, and thymic carcinomas.

The currently used targeted agent for the treatment of diseases associated with both wild-type and mutated KIT is Imatinib mesylate (also known as GLEEVEC or GLIVIC; Novartis, Basel, Switzerland). Imatinib demonstrates activity against certain transmembrane and juxta-membrane KIT mutants, namely F522C and V560G, respectively, but this activity is significantly lowered in common kinase domain mutants, including D816V. See Akin et al. A Novel Form of Mastocytosis Associated with a Transmembrane C-KIT Mutation and Response to Imatinib. Blood. 2004; 103: 3222-3225; Zermati et al. Effect of Tyrosine Kinase Inhibitor STI571 on the Kinase Activity of Wild-type and Various Mutated C-KIT Receptors Found in Mast Cell Neoplasms. Oncogene. 2003; 22: 660-664; Akin et al. Effects of Tyrosine Kinase Inhibitor STI571 on Human Mast Cells Bearing Wild-type or Mutated C-KIT. Exp Hematol. 2003; 31: 686-692; Ma et al. The C-KIT Mutation Causing Human Mastocytosis is Resistant to STI571 and Other KIT Kinase Inhibitors; Kinases with Enzymatic Site Mutations Show Different Inhibitor Sensitivity Profiles than Wild-type Kinases and Those with Regulatory-type Mutations. Blood. 2002; 99: 1741-1744. Other investigational inhibitors of KIT mutated kinases in the art include Dasatinib (Bristol-Myers Squibb (BMS), New York, N.Y.), Midostaurin (also known as PKC412; Novartis, Basel, Switzerland), and Masatinib (also known as AB1010; AB Science, France).

KIT-dependent diseases include diseases characterized by the known KIT mutations D816F, D816H, D816N, D816Y, D816V, K642E, Y823D, Del 550-558, Del 557-561, N822K, V654A, N822H, Del 550-558+V654A, Del557-561+V654A, Ins503AY, V560G, 55bNP, Del557-558, Del W559-560, F522C, Del579, R634W, K642E, T801I, C809G, D820Y, N822K, N822H, Y823D, Y823C and T670I.

SUMMARY OF THE INVENTION

In one embodiment, the present invention includes a method of inhibiting or reducing mutant C-KIT tyrosine kinase activity or expression in a subject suffering from a proliferative disease comprised of identifying the subject having a proliferative disease positive for a constitutively active kinase domain mutant C-KIT or over expression of C-KIT comprising administering to the subject having or suspected to have the proliferative disease, a therapeutically effective amount of a crenolanib compound of Formula I:

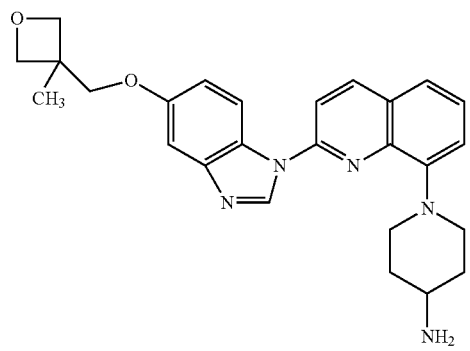 [SMILES: CC1(COc2ccc3c(c2)ncn3-c2ccc3cccc(N4CCC(N)CC4)c3n2)COC1]

or a pharmaceutically acceptable salt or solvate thereof, wherein the C-KIT mutant is at least one of Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT. In one aspect, the compound is provided for a treatment of secondary mutations, wherein secondary mutations is at least one of T670I, V654A, D816V, and N822K. In another aspect, the proliferative disease is selected from at least one of mastocytosis, acute myeloid leukemia, gastrointestinal stromal tumors, sinonasal NK/T-cell lymphoma, seminomas, dysgerminomas, melanomas, and thymic carcinomas. In another aspect, the therapeutically effective amount is from about 15 to 500, 25 to 450, 50 to 400, 100 to 350, 150 to 300, 200 to 250, 15, 25, 50, 75, 100, 150, 200, 250, 300, 400, 450, or 500 mg per day. In another aspect, the compound is administered at least one of continuously, intermittently, systemically, or locally. In another aspect, the mutant C-KIT is defined further as constitutively active. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate. In another aspect, the therapeutically effective amount of compound is administered up to three times or more a day for as long as the subject is in need of treatment for a proliferative disease. In another aspect, the compound is provided at least one of sequentially or concomitantly, with another pharmaceutical agent in a newly diagnosed proliferative disease subject, to maintain remission, or a relapsed/refractory proliferative disease subject. In another aspect, the e compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric subject. In another aspect, the method further comprises the step of determining if the subject is relapsed/refractory to interferon alpha, 2-chlorodoxyadenosine or Imatinib mesylate prior to providing the compound.

In another embodiment, the present invention includes a method for treating a subject suffering from a C-KIT mutated proliferative disease comprising: administering to the subject in need of such treatment a therapeutically effective amount of Crenolanib or a salt thereof, wherein a cell proliferative disorder is characterized by mutant or double mutant C-KIT receptor tyrosine kinase activity and the C-KIT mutated proliferative disease is selected from at least one of a mastocytosis, acute myeloid leukemia, gastrointestinal stromal tumors, sinonasal NK/T-cell lymphoma, seminomas, dysgerminomas, melanomas, and thymic carcinomas, wherein the mutant or double mutant is at least one of: Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT. In one aspect, the compound is provided for the treatment of secondary mutations from at least one of the following mutations T670I, V654A, D816V, and N822K. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate. In another aspect, the therapeutically effective amount of the compound is administered up to three times or more a day for as long as the subject is in need of treatment for proliferative disease. In another aspect, the Crenolanib is provided at least one of sequentially or concomitantly, with another pharmaceutical agent in a newly diagnosed C-KIT mutated proliferative disease, to maintain remission, or a relapsed/refractory C-KIT mutated proliferative disease. In another aspect, the Crenolanib is provided as a single agent or in combination with another pharmaceutical agent for treatment of a pediatric subject with the C-KIT mutated proliferative disease. In another aspect, the Crenolanib is provided as a single agent to at least one of post chemotherapeutic or targeted therapy in newly diagnosed C-KIT mutated proliferative disease. In another aspect, the Crenolanib is provided as a single agent in treatment of subjects with the C-KIT mutated proliferative disease that is either refractory to or has relapsed after treatment with another chemotherapeutic or targeted therapy. In another aspect, the subject is refractory to at least one of interferon alpha, 2 chlorodoxyadenosine or Imatinib mesylate. In another aspect, the method further comprises the step of determining identifying a subject in need of cancer therapy caused by uncontrolled C-KIT tyrosine kinase activity or expression.

In one embodiment, the present invention includes a method of inhibiting or reducing mutant C-KIT tyrosine kinase activity or expression in a subject suffering from a proliferative disease which comprises administering to the subject having or suspected to have the proliferative disease, a therapeutically effective amount of the compound of Formula I:

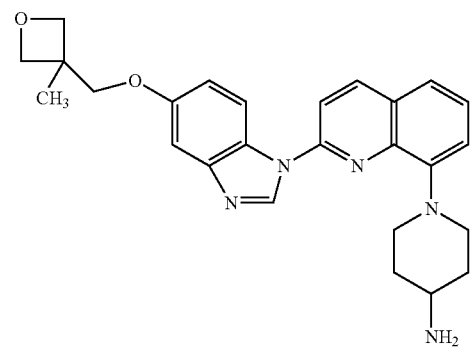 [SMILES: CC1(COc2ccc3c(c2)ncn3-c2ccc3cccc(N4CCC(N)CC4)c3n2)COC1]

or a pharmaceutically acceptable salt or solvate thereof, wherein the C-KIT mutant is at least one of Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT. In one aspect, the compound is provided for the treatment of secondary mutations, wherein secondary mutations is at least one of T670I, V654A, D816V, and N822K. In another aspect, the proliferative disease is selected from at least one of mastocytosis, acute myeloid leukemia, gastrointestinal stromal tumors, sinonasal NK/T-cell lymphoma, seminomas, dysreminomas, melanomas, and thymic carcinomas. In another aspect, the therapeutically effective amounts are from about 15 to 500, 25 to 450, 50 to 400, 100 to 350, 150 to 300, 200 to 250, 15, 25, 50, 75, 100, 150, 200, 250, 300, 400, 450, or 500 mg per day. In another aspect, the compound is administered at least one of continuously, intermittently, systemically, or locally. In another aspect, the mutant C-KIT is defined further as constitutively active. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate. In another aspect, the therapeutically effective amount of compound is administered up to three times or more a day for as long as the subject is in need of treatment for a proliferative disease. In another aspect, the compound is provided at least one of sequentially or concomitantly, with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric subject. In another aspect, the method further comprises the step of determining if the subject is relapsed/refractory to interferon alpha, 2-chlorodoxyadenosine or Imatinib mesylate prior to providing the compound.

In another embodiment, the present invention includes a method for treating a subject suffering from a proliferative disease comprising: administering to the subject in need of such treatment a therapeutically effective amount of Crenolanib or a salt thereof, wherein the cell proliferative disorder is characterized by mutant or double mutant C-KIT receptor tyrosine kinase activity, proliferative disease is selected from at least one of a mastocytosis, acute myeloid leukemia, gastrointestinal stromal tumors, sinonasal NK/T-cell lymphoma, seminomas, dysgerminomas, melanomas, and thymic carcinomas, wherein the mutant or double mutant is at least one of: Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT. In one aspect, the compound is provided for the treatment of secondary mutations from at least one of the following mutations T670I, V654A, D816V, and N822K. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate. In another aspect, the therapeutically effective amount of the compound is administered up to three times or more a day for as long as the subject is in need of treatment for proliferative disease. In another aspect, the Crenolanib is provided at least one of sequentially or concomitantly, with another pharmaceutical agent in a newly diagnosed proliferative disease, to maintain remission, or a relapsed/refractory proliferative disease. In another aspect, the Crenolanib is provided as a single agent or in combination with another pharmaceutical agent for treatment of a pediatric subject with the proliferative disease. In another aspect, the Crenolanib is provided as a single agent to at least one of post chemotherapeutic or targeted therapy in newly diagnosed proliferative disease. In another aspect, the Crenolanib is provided as a single agent in treatment of subjects with the proliferative disease that is either refractory to or has relapsed after treatment with another chemotherapeutic or targeted therapy. In another aspect, the subject is refractory to at least one of interferon alpha, 2 chlorodoxyadenosine or Imatinib mesylate. In another aspect, the method further comprises the step of determining identifying a subject in need of cancer therapy caused by uncontrolled C-KIT tyrosine kinase activity or expression.

The present invention relates to the inhibition of domain mutated KIT and correlates with the treatment of such diseases driven by mutated KIT. The present invention includes a method of inhibiting or reducing mutated C-KIT tyrosine kinase activity or expression in a subject suffering from a proliferative disease driven by mutant C-KIT which comprises administering to the subject having a proliferative disease, a therapeutically effective amount of the compound of Formula I:

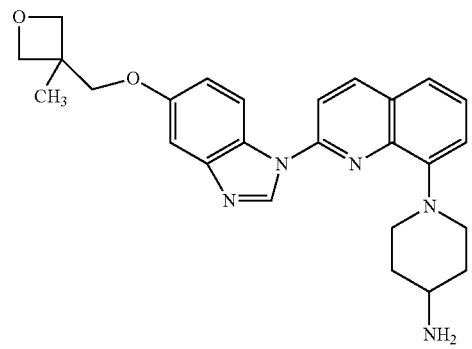 [SMILES: CC1(COc2ccc3c(c2)ncn3-c2ccc3cccc(N4CCC(N)CC4)c3n2)COC1]

or a pharmaceutically acceptable salt or solvate thereof. In one aspect, the therapeutically effective amounts of the present invention are from about 15 to 500 mg per day. In another aspect, the compound is administered at least one of continuously, intermittently, systemically, or locally. In another aspect, the mutated C-KIT is defined further as a mutated C-KIT that is constitutively active. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another aspect, the C-KIT mutation is at least one of D816F, D816H, D816N, D816Y, D816V, K642E, Y823D, Del 550-558, Del 557-561, N822K, V654A, N822H, Del 550-558+V654A, Del557-561+V654A, Ins503AY, V560G, 55bNP, Del557-558, Del W559-560, F522C, Del579, R634W, K642E, T801I, C809G, D820Y, N822K, N822H, Y823D, Y823C and T670I. In another aspect, the therapeutically effective amount of the compound is administered up to three times or more for as long as the subject is in need of treatment for the C-KIT mutant activated proliferative disease. In another aspect, the composition is provided at least one of sequentially or concomitantly, with another pharmaceutical agent in a newly diagnosed proliferative disease subject, or a relapsed/refractory proliferative disease subject. In another aspect, the compound is provided as a single agent or in combination with another pharmaceutical agent in a newly diagnosed proliferative disease subject, or a relapsed/refractory proliferative disease subject. In another aspect, the compound is provided as a single agent or in combination with another pharmaceutical agent in a newly diagnosed proliferative disease pediatric subject, or a relapsed/refractory proliferative disease pediatric subject. In another aspect, the subject is relapsed/refractory to Interferon alpha, 2-chlorodoxyadenosine, or Imatinib Mesylate.

In another embodiment, the present invention includes a method for treating a subject suffering from a C-KIT mutant driven proliferative disease comprising: administering to the subject in need of such treatment a therapeutically effective amount of the present invention or a salt thereof, wherein the cell proliferative disorder is characterized by C-KIT mutant receptor tyrosine kinase activity, the proliferative disease is selected from at least one of mastocytosis, acute myeloid leukemia, gastrointestinal stromal tumors, sinonasal NK/T-cell lymphoma, seminomas, dysgerminomas, melanomas, and thymic carcinomas. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another aspect, the C-KIT mutation is one of D816F, D816H, D816N, D816Y, D816V, K642E, Y823D, Del 550-558, Del 557-561, N822K, V654A, N822H, Del 550-558+V654A, Del557-561+V654A, Ins503AY, V560G, 55bNP, Del557-558, Del W559-560, F522C, Del579, R634W, K642E, T8011, C809G, D820Y, N822K, N822H, Y823D, Y823C and T670I. In another aspect, Crenolanib is provided at least one of sequentially or concomitantly, with another pharmaceutical agent in a newly diagnosed proliferative disease, or a relapsed/refractory proliferative disease. In another aspect, Crenolanib is provided as a single agent or in combination with another pharmaceutical agent for treatment of a pediatric subject with the proliferative disease. In another aspect, Crenolanib is provided as a single agent either concomitantly or sequential with a chemotherapeutic or targeted therapy, in newly diagnosed proliferative disease. In another aspect, Crenolanib is provided as a single agent in treatment of a subject with the proliferative disease that is either refractory to, or has relapsed after, chemotherapeutic or targeted therapy. In another aspect, the subject is refractory to at least one of interferon alpha, 2-chlorodoxyadenosine or Imatinib Mesylate.

The present invention provides methods of reducing or inhibiting the kinase activity of mutant C-KIT in a cell or a subject, and the use of such methods treating cell proliferative disorder (s) driven by mutant C-KIT. Other features and advantages of the invention will be apparent from the following detailed description of the invention and from the claims.

BRIEF DESCRIPTION OF THE DRAWINGS

For a more complete understanding of the features and advantages of the present invention, reference is now made to the detailed description of the invention along with the accompanying figures and in which:

FIG. 20 is a map of the locations of the mutations in relation to the kinase domains of c-kit.

FIGS. 21A and 21B show (FIG. 21A) drug sensitivity tested against BaF3 cell lines expressing mutant c-kit D816V and N882K, with 21B showing the IC50 values for crenolanib shown in FIG. 21A.

DETAILED DESCRIPTION OF THE INVENTION

Figure 1A:
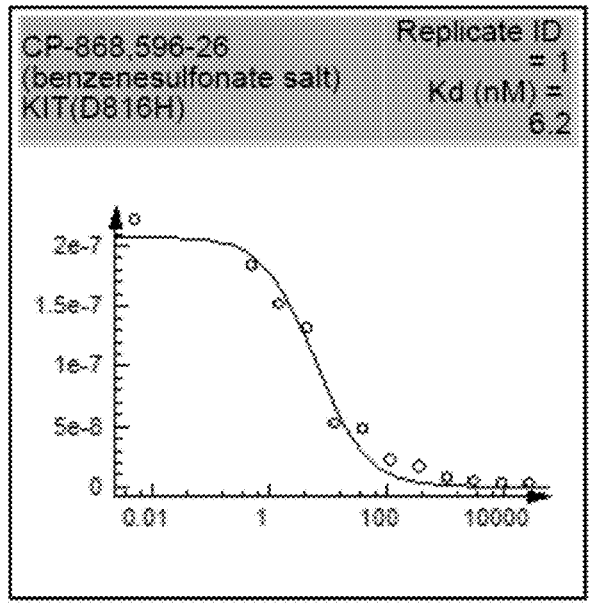
FIGS. 1A and 1B show the replicates of standard dose-response curves for Kd determination of the besylate salt of the present invention for FLT3 D816H (left and right panels are separate replicates). The amount of kinase measured by qPCR (signal; y-axis) is plotted against the corresponding crenolanib concentration in nanomolar in log 10 scale (x-axis).
Figure 1B:
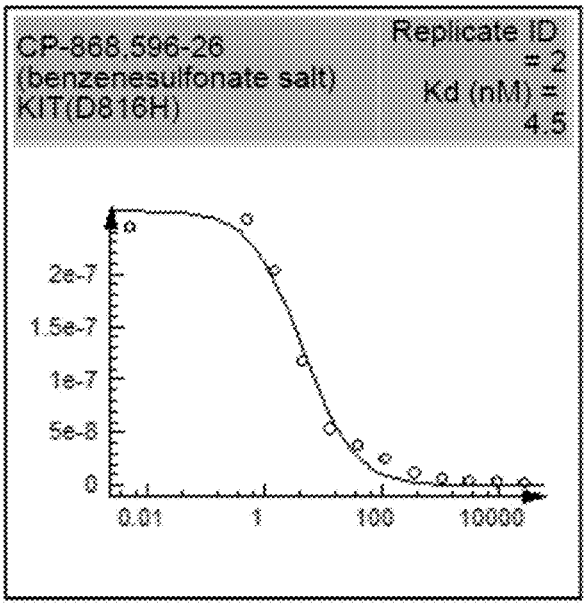
Figure 2A:
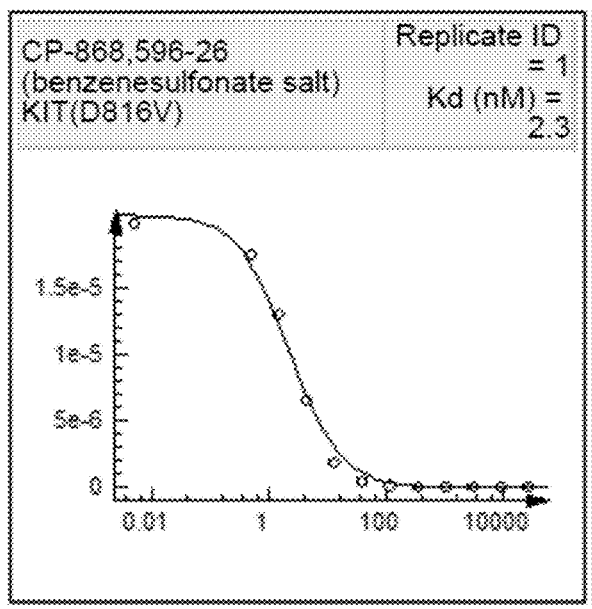
FIGS. 2A and 2B show the replicates of standard dose-response curves for Kd determination of the besylate salt of the present invention for FLT3 D816V (left and right panels are separate replicates). The amount of kinase measured by qPCR (signal; y-axis) is plotted against the corresponding crenolanib concentration in nanomolar in log 10 scale (x-axis).
Figure 2B:
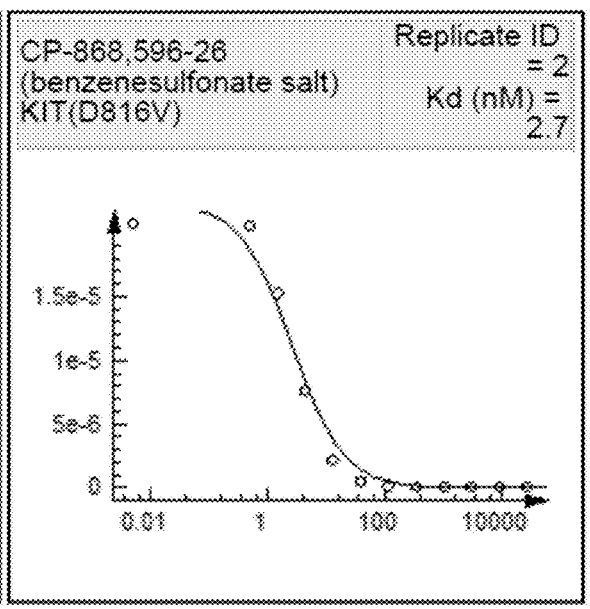

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to inhibit mutant C-KIT kinase activity in a cell or a subject, or to treat disorders related to mutant C-KIT kinase activity or expression in a subject.

In one embodiment to this aspect, the present invention provides a method for reducing or inhibiting the kinase activity of mutant C-KIT in a cell comprising the step of contacting the cell with a compound of the present invention. The present invention also provides a method for reducing or inhibiting the kinase activity of mutant C-KIT in a subject comprising the step of administering a compound of the present invention to the subject. The present invention further provides a method of inhibiting cell proliferation in a cell comprising the step of contacting the cell with a compound of the present invention.

As used herein, the term "subject" refers to an animal, such as a mammal or a human, who has been the object of treatment, observation or experiment.

As used herein, the term "contacting" refers to the addition of the present invention or pharmaceutically acceptable salt to cells such that the compound is taken up by the cell.

In other embodiments to this aspect, the present invention provides therapeutic methods for treating a subject with a cell proliferative disorder driven by aberrant kinase activity of mutant C-KIT.

As used herein, the term "therapeutically effective amount" as used herein, refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Methods for determining therapeutically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorder related to mutant C-KIT," or "disorders related to C-KIT mutated receptor tyrosine kinase," or "mutant C-KIT driven cell proliferative disorder", "C-KIT mutated proliferative disease" or "mutated C-KIT proliferative disease" includes diseases associated with a mutant C-KIT activity, for example, mutations leading to constitutive activation of C-KIT. Examples of "disorders related to mutant C-KIT" include disorders resulting from over stimulation of FLT3 due to mutations in C-KIT.

The term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. Examples of cell proliferative disorders are mastocytosis, acute myeloid leukemia, gastrointestinal stromal tumors, sinonasal NK/T-cell lymphoma, seminomas, dysgerminomas, melanomas, and thymic carcinomas.

In a further embodiment, the present invention can be combined with another therapy as a combination therapy for treating the onset of a cell proliferative disorder related to mutant C-KIT in a subject. The combination therapy comprises the administration of a therapeutically effective amount of a compound of the present invention and one or more other anti-cell proliferation therapies including, but not limited to, chemotherapy and targeted therapy.

In an embodiment of the present invention, a compound of the present invention may be administered in combination with chemotherapy. Used herein, chemotherapy refers to a therapy involving a chemotherapeutic agent. A variety of chemotherapeutic agents may be used in combination with the present invention. By way of example only, taxane compounds, specifically docetaxel, is safely administered in combination with a compound of the present invention in a dosage of 75 mg per square meter (mg/m$^2$) of body surface area.

Chemotherapy is known to those skilled in the art. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. As used herein, the term "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, the term "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention therapeutically effective amounts of the compound having formula I:

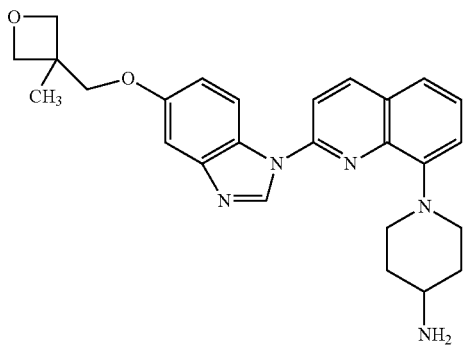 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically effective amount against a proliferative disease is selected from at least one of mastocytosis, acute myeloid leukemia, gastrointestinal stromal tumors, sinonasal NK/T-cell lymphoma, seminomas, dysgerminomas, melanomas, and thymic carcinomas. Pharmaceutically acceptable salts such as hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, and the details of the disease condition. One or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the compounds of the present invention to a patient in need of therapy that includes the compound of Formula I.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and is in no way meant to limit the invention.

Biological Activity.

In Vitro Assays. The following representative in vitro assays were performed in determining the C-KIT biological activity of the present invention. These are given to illustrate the invention in a non-limiting fashion.

Inhibition of mutant C-KIT enzyme activity exemplifies the specific inhibition of the mutant C-KIT enzyme and cellular processes that are dependent on mutant C-KIT activity. All of the examples herein show significant and specific inhibition of mutant C-KIT kinase and C-KIT-dependent cellular responses.

Competitive binding assay. To determine the activity of the present invention in an in vitro kinase assay. Inhibition of the kinase domain of the mutant human C-KIT receptor was performed using the KINOMEscan Kdelect assay protocol. The KINOMEscan platform utilizes a high-throughput competitive binding technology. The assay was performed by combining DNA-tagged kinase, immobilized ligand, and the present invention. The ability of the present invention to compete with immobilized ligand was measured using quantitative PCR of the DNA tag. The competition binding assay was used to evaluate the present invention against a panel of 96 human protein kinases.

Kinase-tagged T7 phage strains were grown in parallel in 24-well blocks in an E. coli host derived from the BL21 strain. E. coli were grown to log phase and infected with T7 phage from a frozen stock and incubated with shaking at 32 degrees Celsius until lysis. The lysates were then centrifuged and filtered. The remaining kinases were produced in HEK-293 cells and tagged with DNA for quantitative PCR detection. Affinity resins for the kinase assay were generated by treating streptavidin-coated magnetic beads with biotinylated small molecule ligands for 30 minutes at room temperature. The liganded beads were blocked with excess biotin and washed with blocking buffer consisting of Sea Block, 1% Bovine Serum Albumin (BSA) 0.05% Tween 20, 1 mM Dithithreitol (DTT) in order to reduce non-specific phage binding. An 11-point 3-fold serial dilution of the present invention was prepared as a 40× stock in 100% Dimethyl sulfoxide (DMSO) and diluted to 1× directly into the assay.

Binding reactions were initiated by combining the liganded affinity beads, kinases, and the present invention in 1× binding buffer consisting of 20% Sea Block, 0.17 Phosphate Buffered Saline (PBS), 0.05% Tween 20, 6 mM DTT. All reactions were performed in polypropylene 384-well plates in a final volume of 0.04 mL. The plates were incubated for 1 hour while shaking at room temperature. The affinity beads were washed with 1×PBS and 0.05% Tween 20 buffer, then re-suspended in elution buffer consisting of 1×PBS, 0.05% Tween 20, 0.5 uM non-biotinylated affinity ligand. Following re-suspension, the affinity beads were incubated at room temperature with shaking. The elutant kinase concentration was then measured by quantitative PCR.

Binding constants (Kds) were calculated with a standard dose-response curve using the Hill equation. Curves were fitted using a non-linear least square fit with the Levenberg-Marquardt algorithm. Kds of the present invention were compared to both a negative DMSO control and a positive control compound. The binding affinity of the present invention was visualized using the compound profile visualization interaction map, TREEspot.

Direct enzyme phosphorylation assay. The Millipore Kinase IC50 Profiler assay was used to screen the present invention against a panel of normal C-KIT and mutated C-KIT kinases. For assays of both kinases, the C-KIT enzyme was incubated with 8 mM of 3-(N-morpholino) propanesulfonic acid (MOPS) at a pH of 7.0, 0.2 mM Ethylenediaminetetraacetic acid (EDTA), 50 uM, a synthetic Abl peptide substrate EAIYAAPFAKKK, 10 mM MgAcetate and [γ-33P-ATP]. The reaction was initiated by the addition of MgATp mix. The reaction mixture was incubated for 40 minutes at room temperature and halted by the addition of 3% phosphoric acid solution. 10 uL of the reaction solution was spotted on P30 filtermat and washed three times in 75 mM phosphoric acid for 5 minutes and then once in methanol prior to drying and scintillation counting. The scintillation values for each replicate, including positive and negative controls, were analyzed using XLFit version 5.1 to determine the IC50 values for the present invention against normal and mutated C-KIT.

Figure 3:
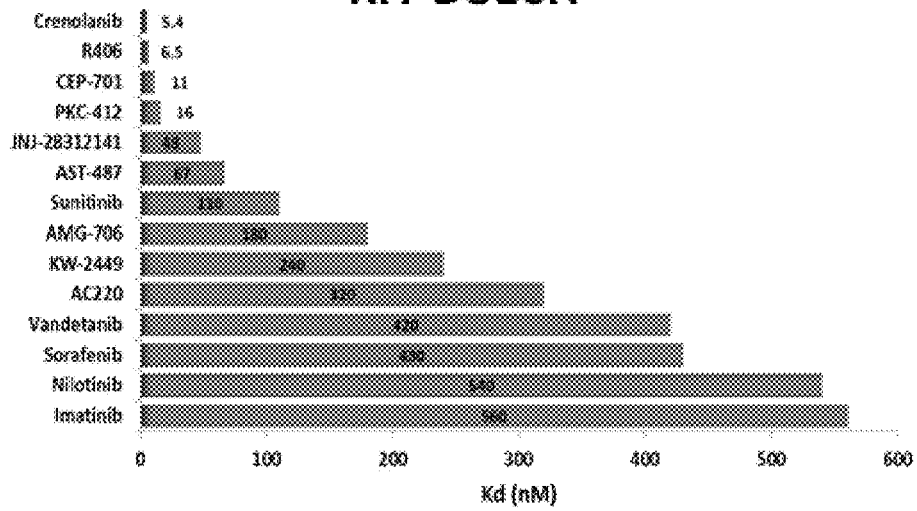
FIG. 3 shows the binding constants of the besylate salt of the present invention compared to other KIT tyrosine kinase inhibitors for the constitutively active KIT D816H mutation.
Figure 4:
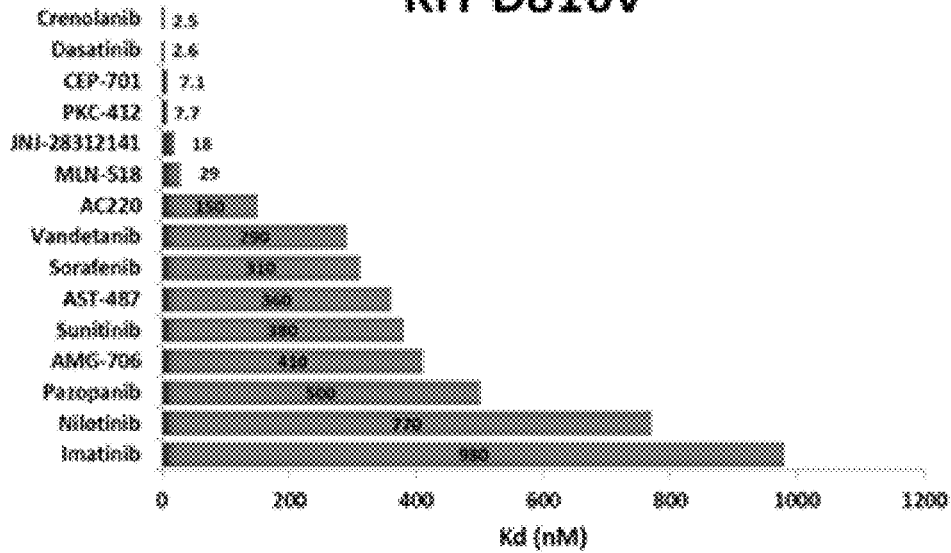
FIG. 4 shows the binding constants of the besylate salt of the present invention compared to other KIT tyrosine kinase inhibitors for the constitutively active FLT3 D816H mutation.

Biological data for the C-KIT-D816 mutation. The activity dose-response curves of the besylate salt of the present invention against C-KIT tyrosine kinase domain mutations D816H and D816V are presented in replicate in FIGS. 1A, 1B and 2A, 2B (left and right panels are separate replicates), respectively. In both FIGS. 3 and 4, the activity of the present invention for the C-KIT D816H and C-KIT D816V mutations is compared against other inhibitors known in the art. All binding constants are presented in nanomolar concentration. See Davis M I, Hunt J P, Herrgard S, et al. Comprehensive analysis of kinase inhibitor selectivity. Nat Biotechnol 2011; 29:1046-51. The binding constant (Kd) of the besylate salt of the present invention for the C-KIT D816H mutation is 5.4 nM and 2.5 nM for the C-KIT D816V mutation. When comparing the Kd of the besylate salt of the present invention for the C-KIT D816H and D816V mutations and other inhibitors in the art, the besylate form of the present invention had a range between one and one hundred three times greater affinity for the C-KIT D816H mutation a range between one and three hundred ninety-two times greater for the C-KIT D816V mutation. Against Imatinib mesylate, the besylate form of the present invention had more than one hundred three times greater affinity for the C-KIT D816H mutation and three hundred ninety-two times more affinity for the C-KIT DB816V mutation than Imatinib Mesylate (D816H Kd=560 nM and D816V Kd=980 nM).

Figure 5:
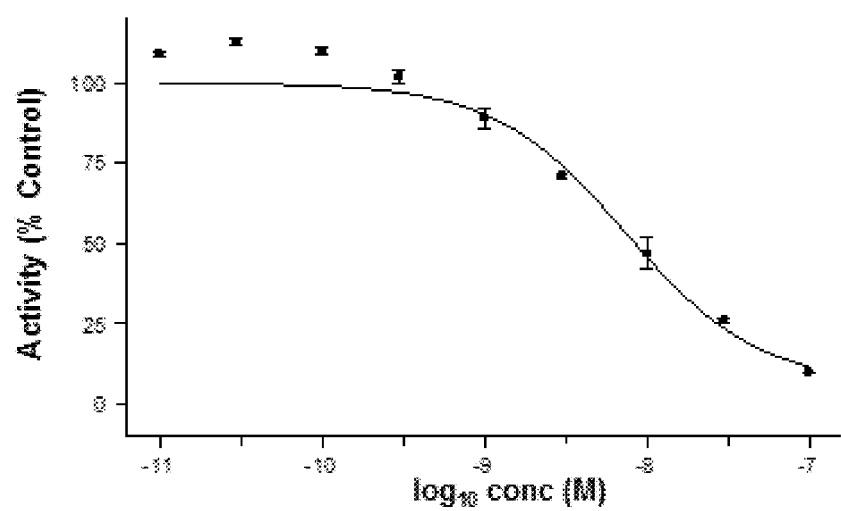
FIG. 5 shows the dose-response curve (n=2) for IC50 determination of the besylate salt of the present invention for FLT3 D835Y. The activity of the besylate salt of crenolanib is plotted against the corresponding molar concentration in log 10 scale.

The activity of the besylate salt of the present invention was determined using a direct enzymatic Millipore IC50 profiler assay. In the direct enzymatic measurement assay, the IC50 of the besylate salt of the current invention against the C-KIT D816H mutation was 7 nM (FIG. 5).

Figure 6:
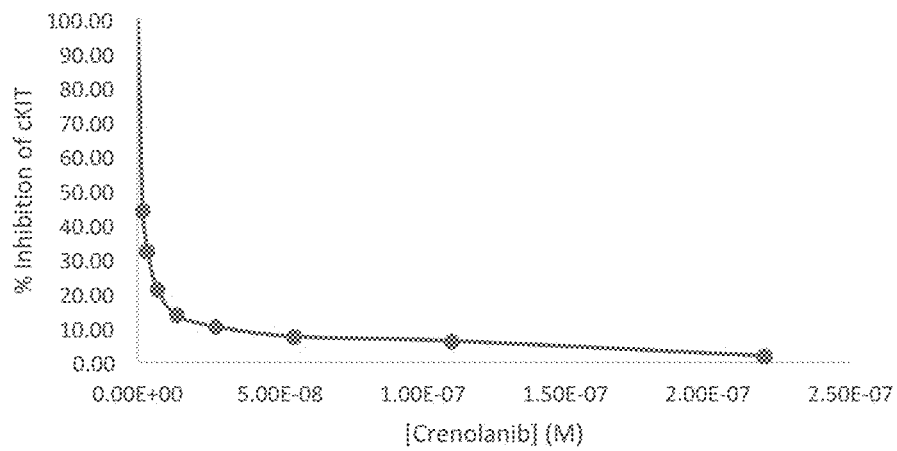
FIG. 6 is a graph that shows the percent inhibition of cKIT(V559A) Enzymatic activity by crenolanib.

FIG. 6 is a graph that shows the percent inhibition of cKIT(V559A) Enzymatic activity by crenolanib.

Figure 7:
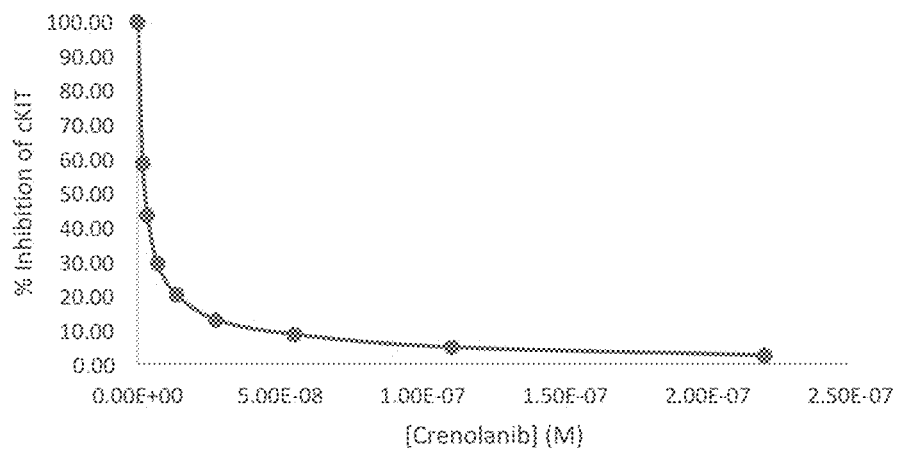
FIG. 7 is a graph that shows the percent inhibition of cKIT(V559D) Enzymatic activity by crenolanib.
Figure 8:
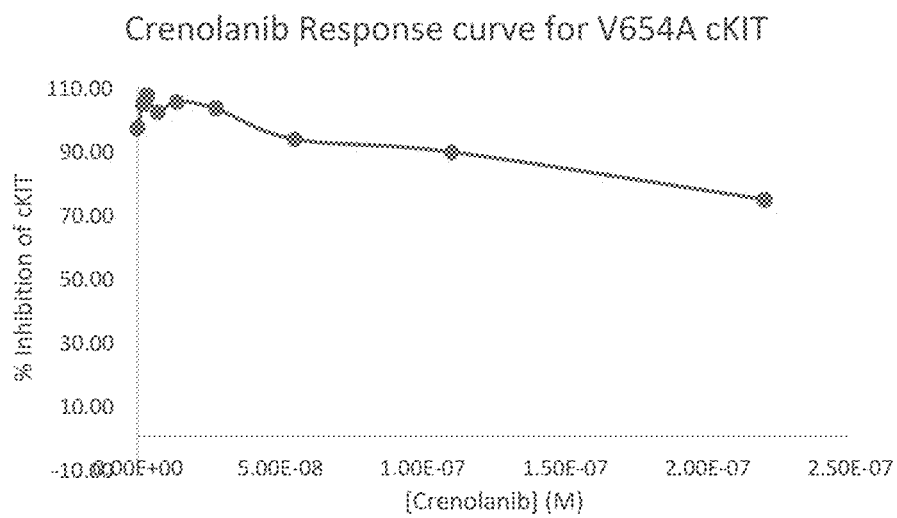
FIG. 8 is a graph that shows the percent inhibition of cKIT(V654A) Enzymatic activity by crenolanib.
Figure 9:
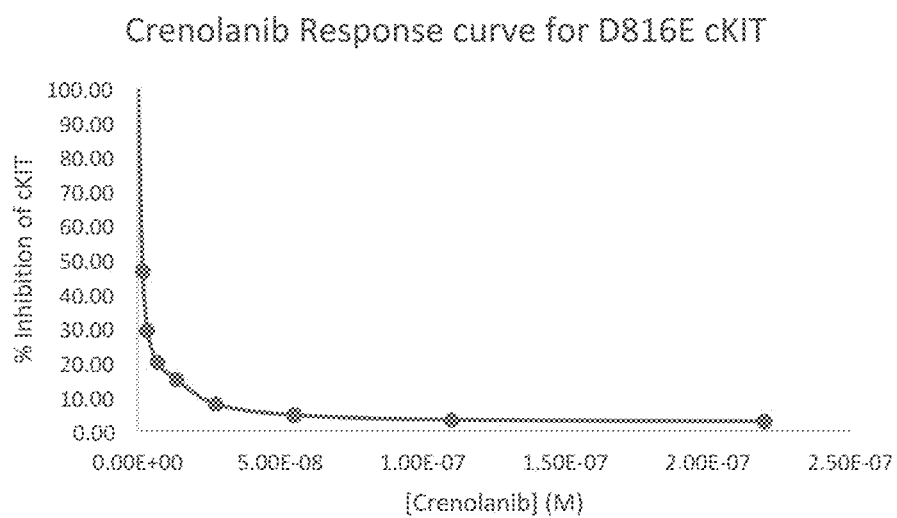
FIG. 9 is a graph that shows the percent inhibition of cKIT(D816E) Enzymatic activity by crenolanib.
Figure 10:
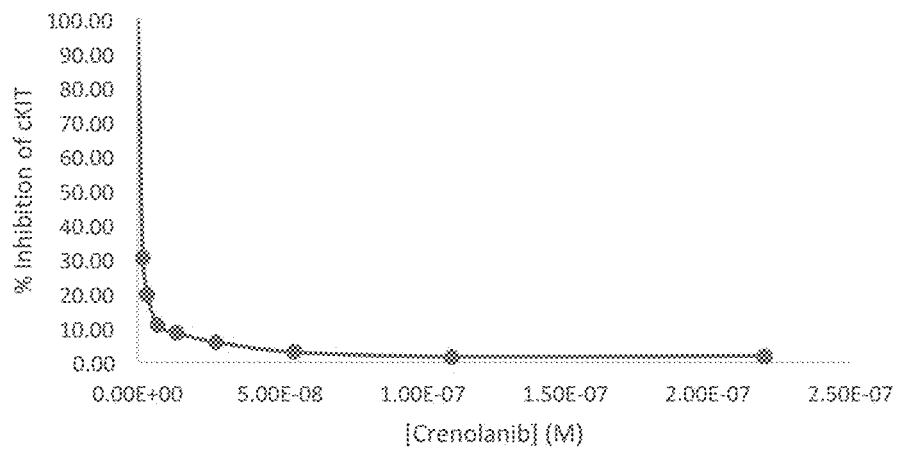
FIG. 10 is a graph that shows the percent inhibition of cKIT(D816I) Enzymatic activity by crenolanib.
Figure 11:
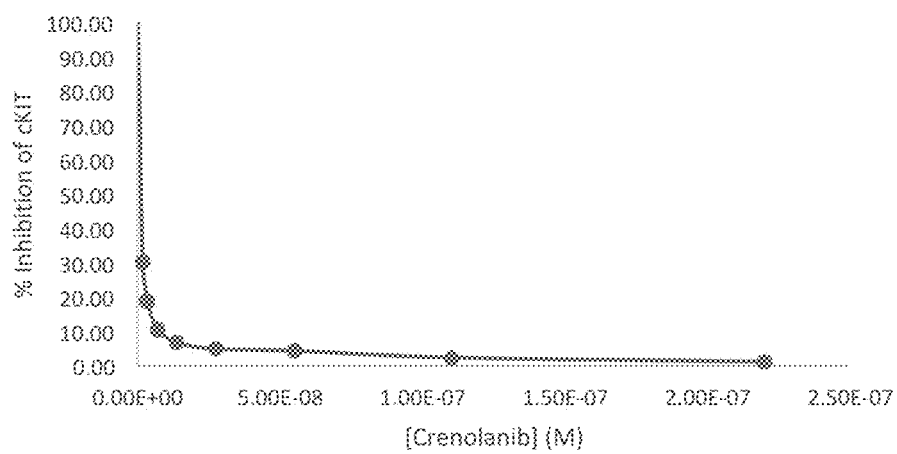
FIG. 11 is a graph that shows the percent inhibition of cKIT(D816V) Enzymatic activity by crenolanib.
Figure 12:
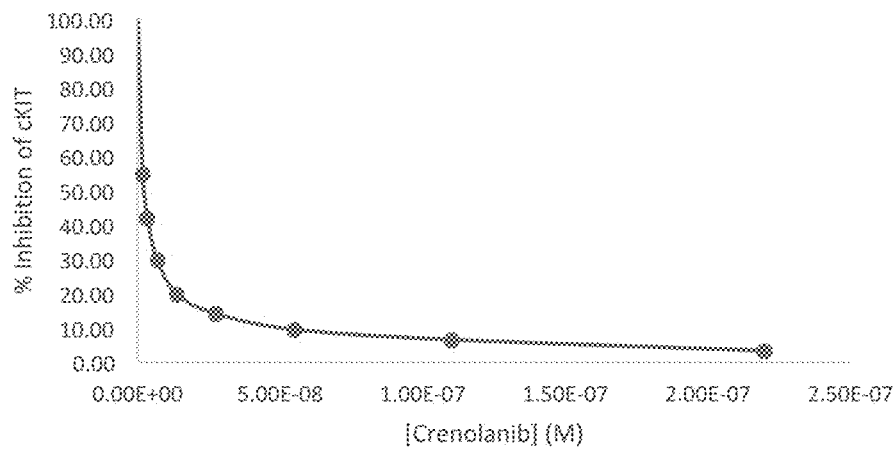
FIG. 12 is a graph that shows the percent inhibition of cKIT(D820E) Enzymatic activity by crenolanib.
Figure 13:
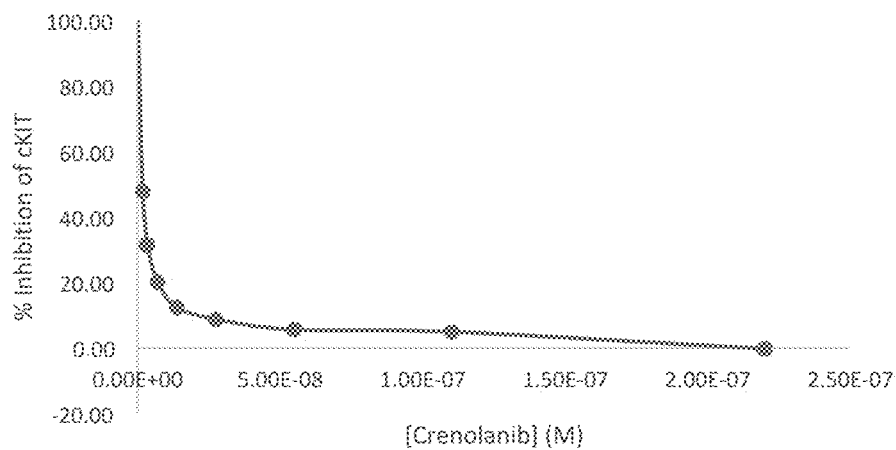
FIG. 13 is a graph that shows the percent inhibition of cKIT(D820V) Enzymatic activity by crenolanib.
Figure 14:
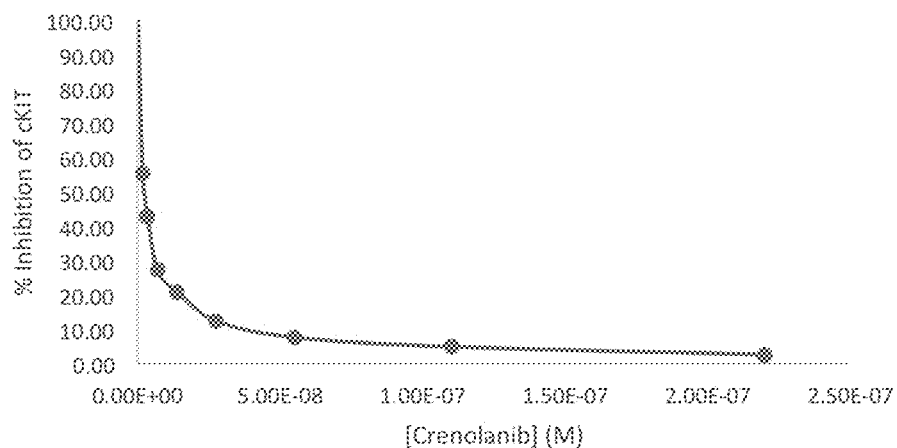
FIG. 14 is a graph that shows the percent inhibition of cKIT(A829P) Enzymatic activity by crenolanib.
Figure 15:
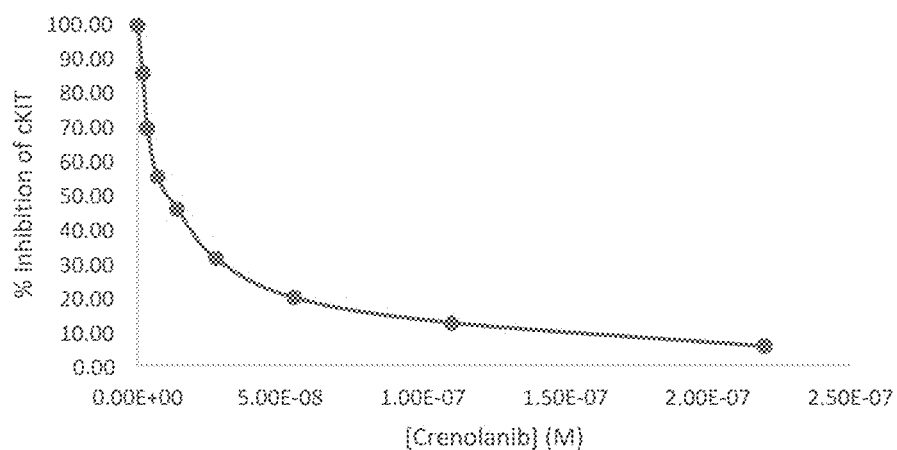
FIG. 15 is a graph that shows the percent inhibition of cKIT(V559D/Y670I) Enzymatic activity by crenolanib.
Figure 16:
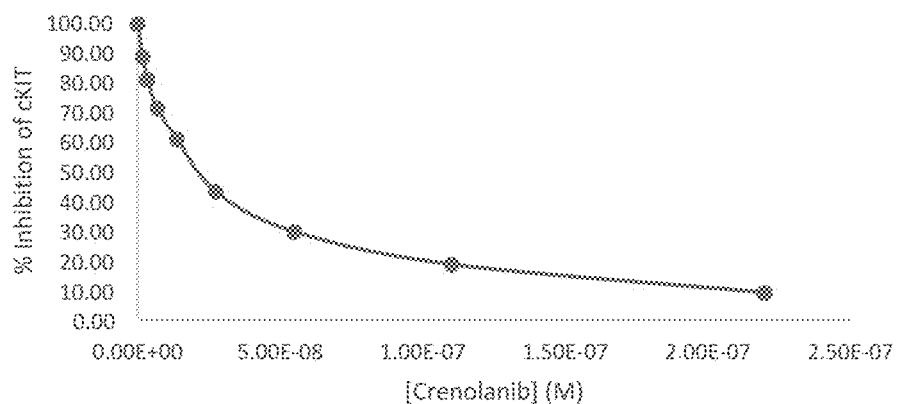
FIG. 16 is a graph that shows the percent inhibition of cKIT(V559D/V654A) Enzymatic activity by crenolanib.
Figure 17:
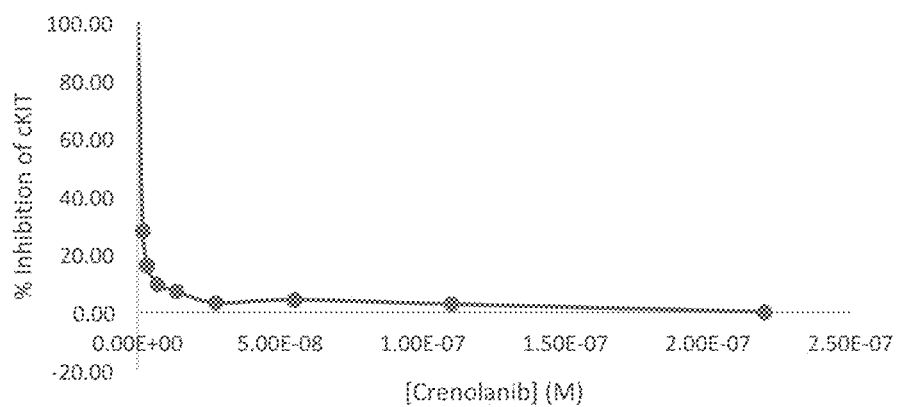
FIG. 17 is a graph that shows the percent inhibition of cKIT(V560G/D816V) Enzymatic activity by crenolanib.
Figures 18, 19:
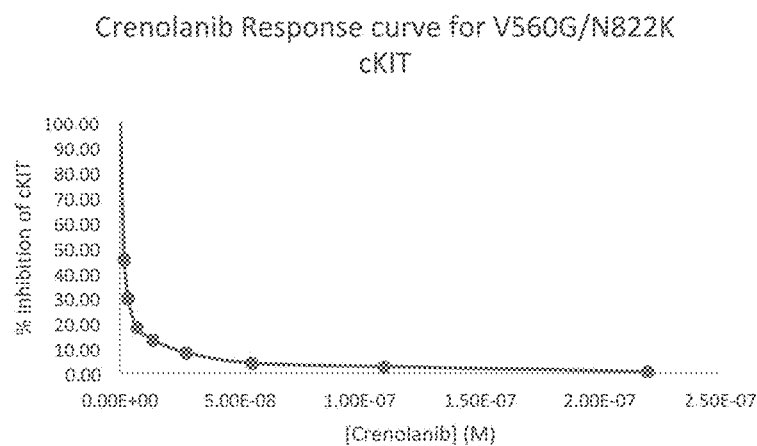
FIG. 18 is a graph that shows the percent inhibition of cKIT(V560G/N882K) Enzymatic activity by crenolanib.
FIG. 19 is a map of the locations of the mutations in relation to the kinase domains of c-kit.

FIG. 7 is a graph that shows the percent inhibition of cKIT(V559D) Enzymatic activity by crenolanib. FIG. 8 is a graph that shows the percent inhibition of cKIT(V654A) Enzymatic activity by crenolanib. FIG. 9 is a graph that shows the percent inhibition of cKIT(D816E) Enzymatic activity by crenolanib. FIG. 10 is a graph that shows the percent inhibition of cKIT(D816I) Enzymatic activity by crenolanib. FIG. 11 is a graph that shows the percent inhibition of cKIT(D816V) Enzymatic activity by crenolanib. FIG. 12 is a graph that shows the percent inhibition of cKIT(D820E) Enzymatic activity by crenolanib. FIG. 13 is a graph that shows the percent inhibition of cKIT(D820V) Enzymatic activity by crenolanib. FIG. 14 is a graph that shows the percent inhibition of cKIT(A829P) Enzymatic activity by crenolanib. FIG. 15 is a graph that shows the percent inhibition of cKIT(V559D/Y670I) Enzymatic activity by crenolanib. FIG. 16 is a graph that shows the percent inhibition of cKIT(V559D/V654A) Enzymatic activity by crenolanib. FIG. 17 is a graph that shows the percent inhibition of cKIT(V560G/D816V) Enzymatic activity by crenolanib. FIG. 18 is a graph that shows the percent inhibition of cKIT(V560G/N882K) Enzymatic activity by crenolanib. FIG. 19 is a map of the locations of the mutations in relation to the kinase domains of c-kit. FIG. 20 is a map of the locations of the mutations in relation to the kinase domains of c-kit. FIGS. 21A and 21B show (FIG. 21A) drug sensitivity tested against BaF3 cell lines expressing mutant c-kit D816V and N882K, with 21B showing the IC50 values for crenolanib shown in FIG. 21A.

Table 1 shows the results with crenolanib besylate in two different assays of a kinase assay measuring activity as measured by % enzyme activity.

|  | % Enzyme Activity (relative to DMSO controls) Crenolanib besylate API | | | IC50 (M) Control | |
| --- | --- | --- | --- | --- | --- |
| Kinases | Data 1 | Data 2 | Average | Cmpd | Control Cmpd ID |
| c-Kit | 93.80 | 93.61 | 93.71 | 1.02E−07 | Staurosporine |
| c-Kit (A829P) | 20.96 | 20.39 | 20.68 | 2.48E−09 | Staurosporine |
| c-Kit (d557-558) | 5.93 | 5.61 | 5.77 | 2.45E−10 | Staurosporine |
| c-Kit (D816E) | 6.65 | 6.54 | 6.60 | 1.36E−10 | Staurosporine |
| c-Kit (D816F) | 11.04 | 9.74 | 10.39 | 2.11E−10 | Staurosporine |
| c-Kit (D816H) | 2.57 | 2.36 | 2.47 | 3.47E−10 | Staurosporine |
| c-Kit (D816I) | 5.27 | 5.16 | 5.22 | 8.48E−10 | Staurosporine |

-continued

| Kinases | % Enzyme Activity (relative to DMSO controls) Crenolanib besylate API | | | IC50 (M) Control | |
|---|---|---|---|---|---|
| | Data 1 | Data 2 | Average | Cmpd | Control Cmpd ID |
| c-Kit (D816V) | 1.47 | 1.10 | 1.29 | 1.63E−10 | Staurosporine |
| c-Kit (D816Y) | 3.91 | 3.39 | 3.65 | 1.93E−10 | Staurosporine |
| c-Kit (D820E) | 9.37 | 9.37 | 9.37 | 8.17E−10 | Staurosporine |
| c-Kit (D820Y) | 4.86 | 3.39 | 4.13 | 2.44E−10 | Staurosporine |
| c-Kit (K642E) | 36.20 | 35.91 | 36.06 | 3.13E−09 | Staurosporine |
| c-Kit (T670I) | 65.23 | 61.78 | 63.50 | 7.43E−09 | Staurosporine |
| c-Kit (V559A) | 6.88 | 6.67 | 6.77 | 1.39E−10 | Staurosporine |
| c-Kit (V559D) | 8.97 | 8.82 | 8.89 | 1.13E−09 | Staurosporine |
| c-Kit (V559D/T670I) | 17.67 | 17.24 | 17.46 | 2.48E−10 | Staurosporine |
| c-Kit (V559D/V654A) | 25.97 | 25.27 | 25.62 | 1.13E−09 | Staurosporine |
| c-Kit (V560G) | 6.97 | 6.60 | 6.78 | 4.43E−10 | Staurosporine |
| c-Kit (V560G/D816V) | 2.99 | 2.49 | 2.74 | 1.47E−10 | Staurosporine |
| c-Kit (V560G/N822K) | 5.71 | 5.19 | 5.45 | 1.77E−10 | Staurosporine |
| c-Kit (V654A) | 91.94 | 90.29 | 91.12 | 1.16E−08 | Staurosporine |
| c-Kit (Y823D) | 13.73 | 13.35 | 13.54 | 8.64E−10 | Staurosporine |
| FMS | 10.94 | 10.04 | 10.49 | 1.27E−09 | Staurosporine |
| PDGF Ra | 13.73 | 13.37 | 13.55 | 4.06E−09 | Staurosporine |
| PDGF Ra (D842V) | 0.20 | −3.56 | −1.68 | 7.32E−10 | Staurosporine |
| PDGF Ra (T674I) | 10.59 | 10.54 | 10.57 | 2.33E−09 | Staurosporine |
| PDGF Ra (V561D) | 9.75 | 9.58 | 9.67 | 5.04E−09 | Staurosporine |
| PDGF Ra-FIP1L1 | 9.62 | 9.10 | 9.36 | 2.78E−09 | Staurosporine |
| PDGF Rb | 11.13 | 11.09 | 11.11 | 2.72E−09 | Staurosporine |
| PDGF Rb-TPM3 | 3.05 | 2.41 | 2.73 | 1.19E−09 | Staurosporine |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Rulina et al., Biochemistry (Moscow). Activated Leukemic Oncogenes AML1-ETO and c-kit: Role of Development of Acute Myeloid Leukemia and Current Approaches for Their Inhibition. 2010; 75(13): 1650-1666.

Tefferi and Pardanani. Targeted Therapy in KIT816V-positive mastocytosis: waiting for proof-of-principle. Leukemia and Lymphoma. March 2010; 51(3): 360-362.

Miettinen et al. KIT (CD117): A Review on Expression in Normal and Neoplastic Tissues, and Mutations and their Clinicopathologic Correlation. Appl Immunohistochem Mol Morphol. 2005; 13: 205-220.

Hug et al. ETO Interacting Proteins. Oncogene. 2004; 23(24): 4270-4274.

Akin et al. A Novel Form of Mastocytosis Associated with a Transmembrane C-KIT Mutation and Response to Imatinib. Blood. 2004; 103: 3222-3225.

Zermati et al. Effect of Tyrosine Kinase Inhibitor STI571 on the Kinase Activity of Wild-type and Various Mutated C-KIT Receptors Found in Mast Cell Neoplasms. Oncogene. 2003; 22: 660-664.

Akin et al. Effects of Tyrosine Kinase Inhibitor STI571 on Human Mast Cells Bearing Wild-type or Mutated C-KIT. Exp Hematol. 2003; 31: 686-692.

Ma et al. The C-KIT Mutation Causing Human Mastocytosis is Resistant to STI571 and Other KIT Kinase Inhibitors; Kinases with Enzymatic Site Mutations Show Different Inhibitor Sensitivity Profiles than Wild-type Kinases and Those with Regulatory-type Mutations. Blood. 2002; 99: 1741-1744.

Davis M I, Hunt J P, Herrgard S, et al. Comprehensive analysis of kinase inhibitor selectivity. Nat Biotechnol 2011; 29:1046-51.

What is claimed is:

1. A method of inhibiting or reducing mutant C-KIT tyrosine kinase activity or expression in a subject suffering from a proliferative disease comprised of identifying the subject having a constitutively active kinase domain mutant C-KIT or over expression of C-KIT that causes a hematological malignancy comprising administering to the subject a therapeutically effective amount of a crenolanib compound of Formula I:

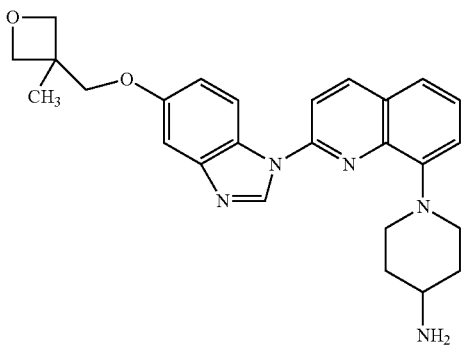 [SMILES: CC1(COc2ccc3c(c2)ncn3-c2ccc3cccc(N4CCC(N)CC4)c3n2)COC1]

or a pharmaceutically acceptable salt or solvate thereof, wherein the C-KIT mutant is at least one of Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT.

2. The method of claim 1, wherein the compound is provided for a treatment of secondary mutations, wherein secondary mutations is at least one of T670I, V654A, D816V, and N822K.

3. The method of claim 1, wherein the therapeutically effective amount is from about 15 to 500, 25 to 450, 50 to 400, 100 to 350, 150 to 300, 200 to 250, 15, 25, 50, 75, 100, 150, 200, 250, 300, 400, 450, or 500 mg per day.

4. The method of claim 1, wherein the compound is administered at least one of continuously, intermittently, systemically, or locally.

5. The method of claim 1, wherein the mutant C-KIT is defined further as constitutively active.

6. The method of claim 1, wherein the compound is administered orally, intravenously, or intraperitoneally.

7. The method of claim 1, wherein the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate.

8. The method of claim 1, wherein the therapeutically effective amount of compound is administered up to three times or more a day for as long as the subject is in need of treatment for the hematological malignancy.

9. The method of claim 1, wherein the compound is provided at least one of sequentially or concomitantly, with another pharmaceutical agent in a newly diagnosed proliferative disease subject, to maintain remission, or a relapsed/refractory hematological malignancy.

10. The method of claim 1, wherein the compound is provided as a single agent or in combination with another pharmaceutical agent in a newly diagnosed proliferative disease subject, to maintain remission, or a relapsed/refractory hematological malignancy.

11. The method of claim 1, wherein the compound is provided as a single agent or in combination with another pharmaceutical agent in a newly diagnosed proliferative disease pediatric subject, to maintain remission, or a relapsed/refractory hematological malignancy.

12. The method of claim 1, further comprising the step of determining if the subject is relapsed/refractory to interferon alpha, 2-chlorodoxyadenosine or Imatinib mesylate prior to providing the compound.

13. A method for treating a subject suffering from a hematological malignancy caused by a mutated C-KIT comprising: administering to the subject in need of such treatment a therapeutically effective amount of Crenolanib or a salt thereof, wherein the hematological malignancy is characterized by mutant or double mutant C-KIT receptor tyrosine kinase activity and the C-KIT mutated proliferative disease is selected from at least one of a mastocytosis, acute myeloid leukemia, gastrointestinal stromal tumors, sinonasal NK/Tcell lymphoma, seminomas, dysgerminomas, melanomas, and thymic carcinomas, wherein the mutant or double mutant is at least one of: Del 557-558, V559A, V559D, K642E, V560G, V654A, T670I, D816E, D816I, D816V, D820E, D820Y, D820V, N822H, N822K, Y823C, Y823D, A829P, V559D/T670I, V559D/V654A, V560G/D816V, and V560G/N822K mutant C-KIT.

14. The method of claim 13, wherein the compound is provided for the treatment of secondary mutations from at least one of the following mutations T670I, V654A, D816V, and N822K.

15. The method of claim 13, wherein the compound is administered orally, intravenously, or intraperitoneally.

16. The method of claim 13, wherein the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate or Crenolanib Succinate.

17. The method of claim 13, wherein the therapeutically effective amount of the compound is administered up to three times or more a day for as long as the subject is in need of treatment for the hematological malignancy.

18. The method of claim 13, wherein the Crenolanib is provided at least one of sequentially or concomitantly, with another pharmaceutical agent in a newly diagnosed C-KIT mutated proliferative disease, to maintain remission, or a relapsed/refractory C-KIT mutated hematological malignancy.

19. The method of claim 13, wherein the Crenolanib is provided as a single agent or in combination with another pharmaceutical agent for treatment of a pediatric subject with the C-KIT mutated hematological malignancy.

20. The method of claim 13, wherein the Crenolanib is provided as a single agent to at least one of post chemotherapeutic or targeted therapy in newly diagnosed C-KIT mutated hematological malignancy.

21. The method of claim 13, wherein the Crenolanib is provided as a single agent in treatment of subjects with the C-KIT mutated proliferative disease that is either refractory to or has relapsed after treatment with another chemotherapeutic or targeted therapy.

22. The method of claim 13, wherein the subject is refractory to at least one of interferon alpha, 2 chlorodoxyadenosine or Imatinib mesylate.

23. The method of claim 13, further comprising the step of determining identifying a subject in need of cancer therapy caused by uncontrolled C-KIT tyrosine kinase activity or expression.

* * * * *